United States Patent
Bartley et al.

(10) Patent No.: US 11,749,924 B2
(45) Date of Patent: Sep. 5, 2023

(54) ELECTRICAL CONNECTOR FOR A MEDICAL PATCH SENSOR

(71) Applicant: AVX Corporation, Fountain Inn, SC (US)

(72) Inventors: Shelby Bartley, Simpsonville, SC (US); Jeffrey Cain, Greenville, SC (US); Joseph M. Hock, Surfside Beach, SC (US)

(73) Assignee: KYOCERA AVX Components Corporation, Fountain Inn, SC (US)

( * ) Notice: Subject to any disclaimer, the term of this patent is extended or adjusted under 35 U.S.C. 154(b) by 0 days.

(21) Appl. No.: 17/356,639

(22) Filed: Jun. 24, 2021

(65) Prior Publication Data
US 2022/0013943 A1  Jan. 13, 2022

Related U.S. Application Data

(60) Provisional application No. 63/049,146, filed on Jul. 8, 2020.

(51) Int. Cl.
| | |
|---|---|
| H01R 12/00 | (2006.01) |
| H01R 12/88 | (2011.01) |
| H01R 12/81 | (2011.01) |
| H01R 12/77 | (2011.01) |
| H01R 43/26 | (2006.01) |
| A61B 5/00 | (2006.01) |
| H01R 12/70 | (2011.01) |
| H01R 13/635 | (2006.01) |

(52) U.S. Cl.
CPC .......... *H01R 12/88* (2013.01); *A61B 5/6833* (2013.01); *H01R 12/774* (2013.01); *H01R 12/81* (2013.01); *H01R 43/26* (2013.01); *A61B 2562/227* (2013.01); *H01R 12/7023* (2013.01); *H01R 13/635* (2013.01); *H01R 2201/12* (2013.01)

(58) Field of Classification Search
CPC ......... H01R 12/79; H01R 12/78; H05K 3/365
See application file for complete search history.

(56) References Cited

U.S. PATENT DOCUMENTS 8,939,790 B2 * 1/2015 Jung .................... H01R 12/774
439/495

OTHER PUBLICATIONS

Cheng et al., "Wearable Sensor Patch for Early Extravasation Detection," *2016 IEEE 66th Electronic Components and Technology Conference*, 2016, pp. 1631-1637.

* cited by examiner

*Primary Examiner* — Phuong Chi Thi Nguyen
(74) *Attorney, Agent, or Firm* — Dority & Manning, P.A.

(57) ABSTRACT

A medical sensor patch connector assembly can include a medical patch having a first side, a second side opposite the first side, and a hole connecting the first side and the second side. The medical sensor patch connector assembly can include a connector including a first clamping member having a first contact surface in contact with the first side of the medial patch and a tab protruding through the hole in the medical patch. The connector can include a second clamping member having a second contact surface in contact with the second side of the medical patch.

19 Claims, 4 Drawing Sheets

ELECTRICAL CONNECTOR FOR A MEDICAL PATCH SENSOR

CROSS REFERENCE TO RELATED APPLICATION

The present application claims filing benefit of U.S. Provisional Patent Application Ser. No. 63/049,146 having a filing date of Jul. 8, 2020, which is incorporated herein by reference in its entirety.

BACKGROUND OF THE INVENTION

Medical sensor patches can be adhered to a patient's skin to sense various characteristics of the patient's skin. Such medical sensor patches can require electrical connection with sensing equipment. Movement of the patient, however, can strain the connection between the medical sensor patch. Such strain can cause the medical sensor patch to become electrically disconnected from the sensing equipment.

SUMMARY OF THE INVENTION

In accordance with one embodiment of the present invention, a medical sensor patch connector assembly can include a medical patch having a first side, a second side opposite the first side, and a hole connecting the first side and the second side. The medical sensor patch connector assembly can include a connector including a first clamping member having a first contact surface in contact with the first side of the medial patch and a tab protruding through the hole in the medical patch. The connector can include a second clamping member having a second contact surface in contact with the second side of the medical patch.

In accordance with another embodiment of the present invention, a medical sensor patch connector can include a first clamping member including a first contact surface and a tab protruding perpendicular with respect to the first contact surface; a second clamping member including a second contact surface and a hinged connection with the first clamping member such that the first contact surface can be arranged opposite and parallel with the second contact surface. The tab of the first clamping member can be configured to protrude through a hole in a medical patch to retain the medical patch between the first contact surface and the second contact surface in which at least one of the first contact surface of the first clamping member or the second contact surface of the second clamping member contacts the medical sensor patch.

In accordance with another embodiment of the present invention, a method of forming a medical sensor patch connector assembly can include providing a first clamping member including a first contact surface and a tab protruding perpendicularly with respect to the first contact surface; attaching a second clamping member to the first clamping member at a hinged connection such that a first contact surface of the first clamping member can be arranged opposite and parallel with a second contact surface of the second clamping member and such that the tab of the first clamping member extends perpendicular to the second contact surface; arranging a medical patch between the first contact surface and second contact surface; and moving the first clamping member towards the second clamping member such that the tab of the of the first clamping member extends through the hole of the medical patch.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figure in which.

Figure 1:
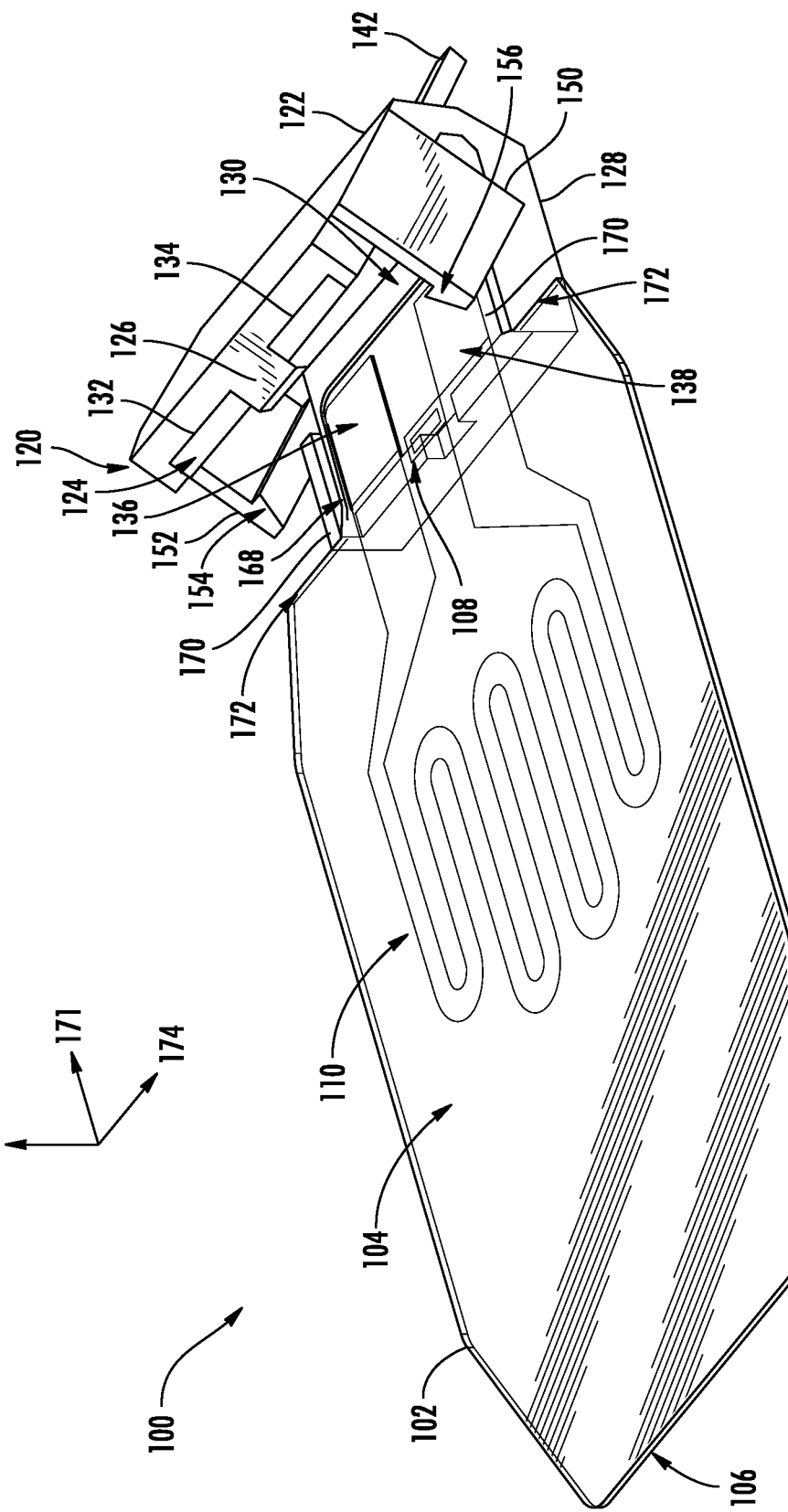
FIG. 1 illustrates an embodiment of a medical sensor patch connector assembly including a connector in a partially open configuration and a medical patch.

Repeat use of reference characters in the present specification and drawing is intended to represent same or analogous features or elements of the invention.

DETAILED DESCRIPTION OF REPRESENTATIVE EMBODIMENTS

It is to be understood by one of ordinary skill in the art that the present discussion is a description of exemplary embodiments only, and is not intended as limiting the broader aspects of the present invention, which broader aspects are embodied in the exemplary construction.

Generally speaking, the present invention is directed to an electronical connector for a medical patch sensor. The electrical connector can be configured selectively couple with the medical patch sensor and provide electrical connection with the medical patch sensor. The electrical connector can include a tab configured to engage a hole in the medical patch sensor such that the medical patch sensor is more securely coupled with the electrical connector.

For example, in some implementations, a medical sensor patch connector assembly can include a medical patch having a first side, a second side opposite the first side, and hole connecting the first side and the second side. The medical sensor patch connector assembly can include a connector including a first clamping member and a second clamping member. The first clamping member can have a first contact surface in contact with the first side of the medial patch and a tab protruding through the hole in the medical patch. The tab can protrude in a direction that is perpendicular to the contact surface of the first clamping member. The second clamping member can have a second contact surface in contact with the second side of the medical patch. The second clamping member can be pivotally coupled to the first clamping surface at a coupling location of the first clamping member.

The second clamping member can include a receiving feature engaged with the tab of the first clamping member. The first contact surface and/or the second contact surface of the connector can include one or more conductive layers that are in contact with the medical patch. The conductive layers can facilitate electrical connection with one or more conductive traces of the medical patch to facilitate electrical connection with the conductive trace(s) to other electrical components, for example by lead wires.

The connector can include a first conductive trace in contact with the first conductive trace of the medical patch and a second conductive trace in contact with the second conductive trace of the medical patch. For example, a first conductive layer of the component can contact a first portion of the conductive trace of the medical patch. A second conductive layer of the connector can contact a second portion of the conductive trace of the medical patch such that an electrical characteristic (e.g., resistance, capacitance, impedance, etc.) can be detected for the conductive trace between the first portion and second portion of the conductive trace.

One or more lead wires may facilitate electrical connection with the conductive trace of the medical patch. For example, a first lead wire may be coupled to the first conductive trace of the connector. A second lead wire may be coupled to the second conductive trace of the connector.

In some embodiments, the lead wires may be integrally formed with the connector (e.g., with respective conductive layers). For instance, the lead wires may extend as respective portions of the conductive layers of the connector. As another example, the lead wires can be soldered, brazed or otherwise affixed to the respective conductive layers of the connector. In yet further embodiments, the lead wires can be mechanically coupled with the conductive layers of the connector. For instance, the connector can include one or more holes for receiving the lead wires therein. The connector can include one or more mechanical crimping or clamping devices to secure the wires to respective conductive layers of the connector. The wires can be selectively removable with respect to the connector such that the connector can be reusable. In other embodiments, however, the connector can be single use. Once coupled with the medical patch the connector may be difficult to de-couple from the medical patch without damaging the medical patch or connector. This can prevent repeat use, for example, where repeat use would be unsanitary, unsafe, or otherwise undesirable.

In some embodiments, the connector can include a hinged connection between the first clamping member and the second clamping member. For example, the hinged connection can include a thin, flexible layer of material connecting the first clamping member and the second clamping member. As another example, the hinged connection can include a mechanical hinge (e.g., a Mortise hinge, barrel hinge, piano hinge, or any other suitable type of hinged configuration.

In some embodiments, the connector can include a resilient member arranged and sized such that the resilient member is compressed when the connector is in the closed configuration. The compression of the resilient member can cause the resilient member to exert an opening force against at least one of the first clamping member or the second clamping member. The compression of the resilient member can increase pressure and/or friction between the first clamping member and the medical patch and/or between the second clamping member and the medical patch when the connector is in the closed configuration. Such increased pressure and/or friction can improve the ability of the connector to retain the medical patch in the connector.

The connector may include a variety of suitable materials. For example, the connector can include thermoset materials, thermoplastics materials, resins, or other suitable materials. The various conductive layers can be or include a variety of suitable conductive materials, such as copper, nickel, tin, gold, and the like. The resilient member can be or include a variety of compressible and/or resilient materials, such as closed-cell foams (e.g., polyethylene foams, cross-linked polyethylene foam (XLPE), and/or reticulated polyurethane.

The various components of the connector can be formed using a variety of suitable techniques. For example, the clamping members can be injection molded and assembled (e.g., snapped together without adhesive and/or adhered together with a suitable adhesive). Various features of the connector (e.g., guide rails, hinge members, etc.) can be over-molded onto base components (e.g., clamping members).

I. Example Embodiments

Figure 2:
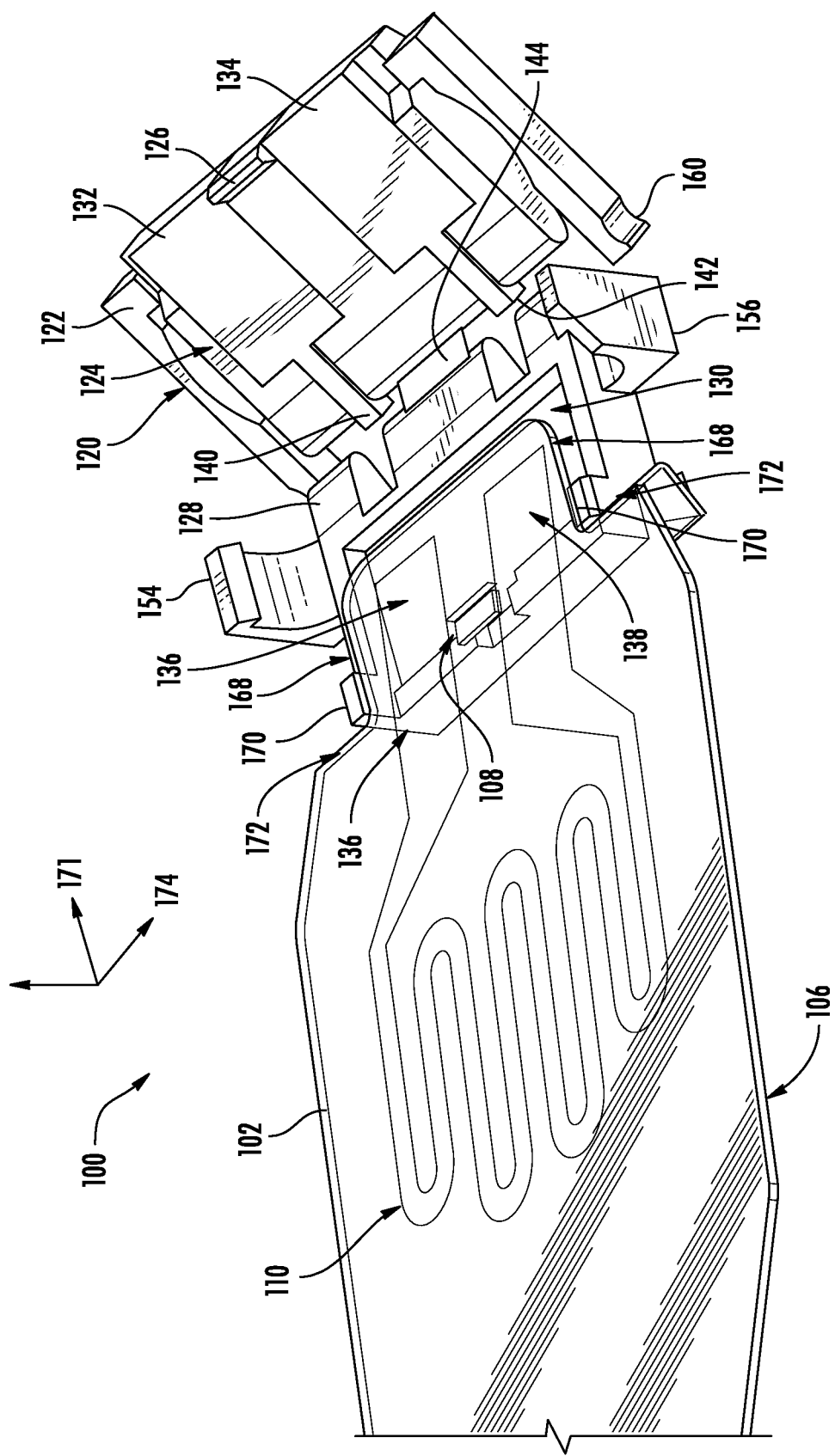
FIG. 2 illustrates another embodiment of a medical sensor patch connector assembly including a connector in a partially open configuration and a medical patch.
Figure 3:
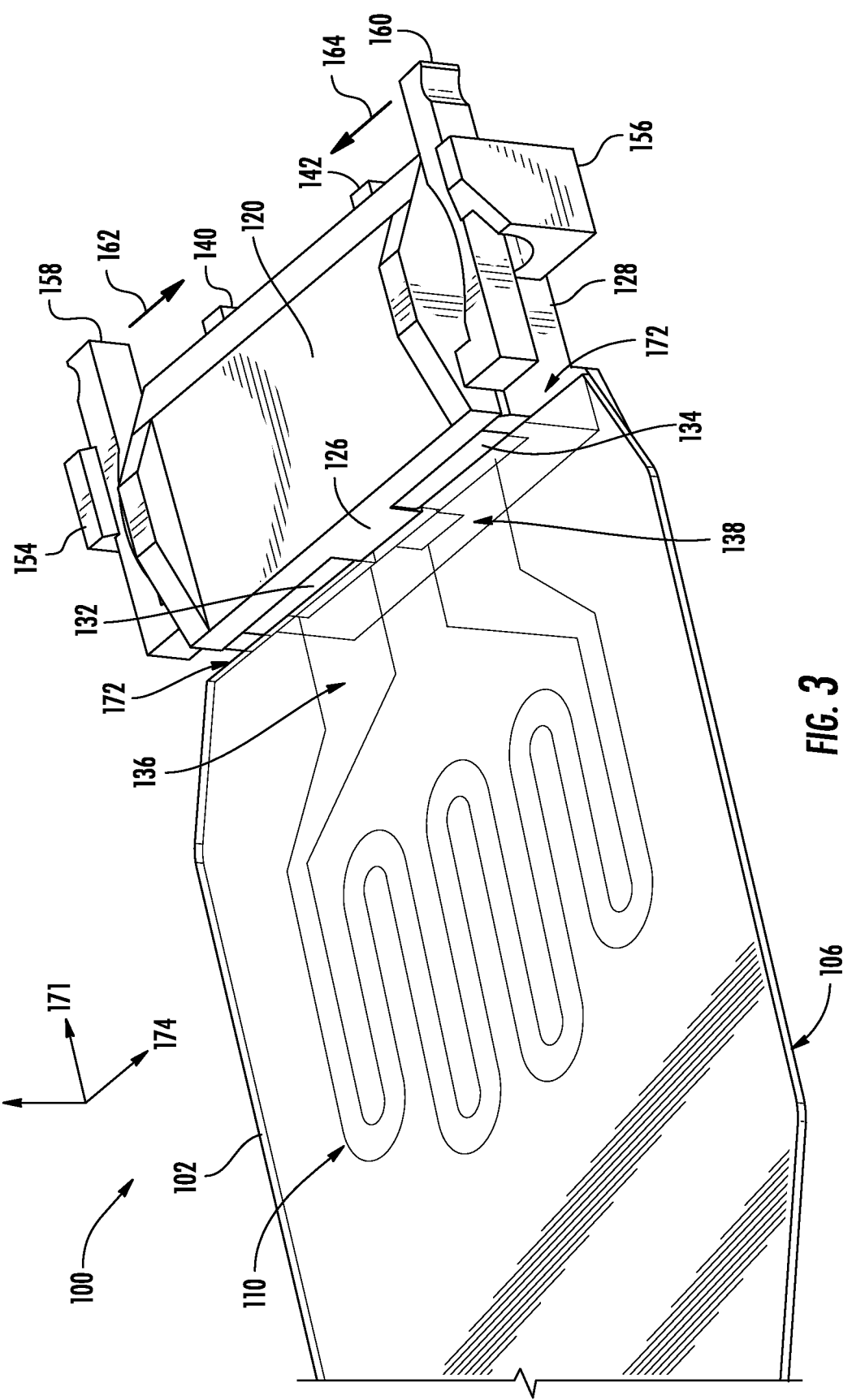
FIG. 3 illustrates the medical sensor patch connector assembly of FIG. 2 in a closed configuration.

FIG. 1 illustrates an embodiment of a medical sensor patch connector assembly 100 in a partially open configuration. FIG. 2 illustrate another embodiment of a medical sensor patch connector assembly 200 in a partially open configuration. FIG. 3 illustrates the embodiment of the medical sensor patch connector assembly 300 of FIG. 2 in a closed configuration. Reference numerals are used in FIGS. 1, 2, and 3 to refer to similar features.

Referring to FIG. 1, a medical patch 102 can have a first side 104, a second side 106 opposite the first side 104. For example, the medical patch 102 can be or include a thin film or layer. The medical patch 102 can be adhered to a skin surface, for example to detect extravasation due to an injection. The medical patch 102 can include a hole 108 connecting the first side 104 and the second side 106. The medical patch 102 can include a conductive trace 110 (e.g., on the first side 104, second side 106, and/or disposed within the medical patch 102).

A connector 120 can be configured to engage and retain the medical patch 102. The connector 120 can include a first clamping member 122 having a first contact surface 124 configured to contact the first side 104 of the medial patch 102 when the connector 120 is in a closed configuration, for example as described below with reference to FIG. 3. The first clamping member 122 can include a tab 126 configured to protruded through the hole 108 in the medical patch 102 when the connector 120 is in the closed configuration.

The connector 120 can include a second clamping member 128 having a second contact surface 130 configured to contact the second side 106 of the medical patch 102 when the connector 120 is in the closed configuration. The second clamping member 128 can be configured to engage with the tab 126 of the first clamping member 122 to retain the connector 120 in the closed configuration.

The connector 120 can include one or more conductive layers 132, 134 configured to contact the conductive layer medical patch 102 in the closed configuration. The first contact surface 124 or the second contact surface 130 of the connector 120 can include the conductive layers 132, 134.

The conductive trace 110 of the medical patch 102 can include a first portion 136 and a second portion 138. The first portion 136 of the conductive trace 110 of the medical patch 102 can contact the first conductive layer 132. The second portion 138 of the conductive trace 110 of the medical patch 102 can contact the second conductive layer 134.

A first lead wire 140 (FIGS. 2 and 3) may be coupled with the first conductive layer 132 of the connector 120. A second lead wire 142 (FIGS. 2 and 3) may be coupled to the second conductive layer 134 of the connector. When the connector 120 is in the closed configuration (for example as described below with reference to FIG. 3), the first conductive layer 132 of the connector 120 can contact the first portion 136 of the conductive trace 110 of the medical patch 102. The second conductive layer 134 of the connector 120 can contact the second portion 138 of the conductive trace 110 of the medical patch 102.

The connector 120 can include a hinged connection 144 between the first clamping member 122 and the second clamping member 128. For example, the hinged connection 144 can include a thin, flexible layer of material connecting the first clamping member 122 and the second clamping member 128. As another example, the hinged connection 144 can include a mechanical hinge (e.g., a Mortise hinge, barrel hinge, piano hinge, or any other suitable type of hinged configuration. One example hinged connection is described below with reference to FIG. 4.

The medical sensor patch connector assembly 100 can include a variety of latching mechanisms. For example, referring to FIG. 1, in some embodiments, the first clamping member 122 can include one or more arms 150, 152 configured to engage the second clamping member 128 and retain the medical sensor patch connector assembly 100 in the closed configuration, for example as described with reference to FIG. 3. More specifically, the arms 150, 152 can include respective protrusions 154, 156. The arms 150, 152 and protrusions 154, 156 can be sized and configured to engage the second clamping member 128 and retain the second clamping member 128 in the closed configuration such that the medical patch 102 is secured in the connector 120, for example, by the tab 126 protruding through the hole 108 in the medical patch 102.

As another example latching mechanisms, referring to FIG. 2, the second clamping member 128 can include protrusions 154,156 configured to engage the first clamping member 122 and retain the medical sensor patch connector assembly 100 in the closed configuration, for example as described with reference to FIG. 3.

Figure 4:
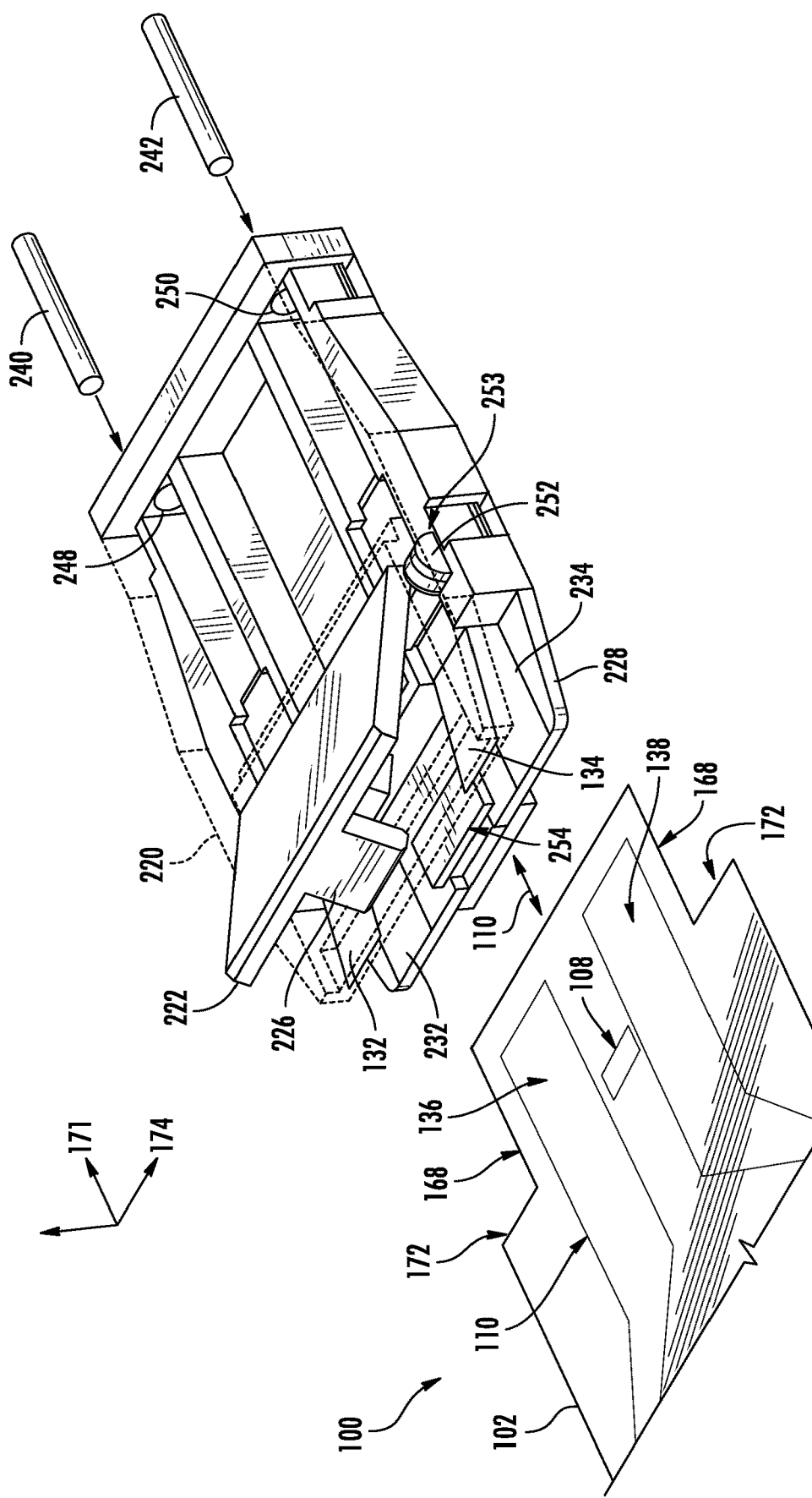
FIG. 4 illustrates another example medical sensor patch connector assembly according to aspects of the present disclosure.

In some embodiments, the medical sensor patch connector assembly 100 can include a variety of release mechanisms to open the medical sensor patch connector assembly 100 from the closed configuration (e.g., to remove the medical patch 102 from the medical sensor patch connector assembly 100). Referring to FIGS. 3 and 4, the medical sensor patch connector assembly 100 can include one or more release levers 158, 160. In this example configuration, forcing the levers 158, 160 inwards towards each other as illustrated by arrows 162 in FIG. 3 (for example with a pinching movement) can disengage the protrusions 154, 156 of the second clamping member 128. Once the protrusions 154, 156 are disengaged, the second clamping member 128 can be pivoted relative to the first clamping member 122 to open the medical sensor patch connector assembly 100 form the closed configuration such that the medical patch 102 can be removed from the connector 120.

In some embodiments, the medical patch 102 can include a tab 126 defining the portions 136, 138 of the medical patch 102 that are in contact with the first contact surface 124 and the second contact surface 130. The tab 126 can have opposite edges 168 (e.g., extending in an insertion direction 171). The connector 120 (e.g., second clamping member 128) can include one or more guide rails 170 sized relative to the opposite edges 168 to align the tab 126 in the cross-insertion direction 174 such that the protrusion 126 is aligned with the hole 108 in the medical patch 102 (e.g., in the cross-insertion direction 174).

In some embodiments the medical patch 102 can include one or more boss edges 172 (e.g., aligned with the cross-insertion direction 171) that are configured to align the tab 126 (e.g., in the insertion direction 171) such that the protrusion 126 is aligned with the hole 108 (e.g., in the insertion direction 171). The boss edges 172 can be perpendicular to the opposite edges 168. For example, the tab 126 and connector 120 can be sized such that the boss edges 172 align the protrusion 126 with the hole 108 (e.g., in the insertion direction 171) when the tab is fully inserted into the connector 120 such that the boss edges 172 contact the connector 120.

FIG. 4 illustrates another example medical sensor patch connector assembly 200 according to aspects of the present disclosure. A connector 220 can include a first clamping member 222 and second clamping member 228. The first clamping member 222 can include a tab 226 configured to protruded through the hole 108 in the medical patch 100 when the connector 220 is in the closed configuration to retain the medical patch 100 in the connector 220. The second clamping member 228 can include a first conductive layer 232 and a second conductive layer 234 configured to contact the first portion 136 and the second portion 138, respectively, of the conductive trace 110 of the medical patch 100. In this example embodiment, first and second lead wires 240, 242 can be inserted into respective receiving holes 248, 250 of the connector 220 until the lead wires 240, 242 respectively contact conductive layers 232, 234 of the connector 220. Thus, the connector 220 can facilitate electrical connection between the first lead wire 240 with the first portion 136 of the conductive trace 110 of the medical patch 102. The connector 220 can facilitate electrical connection between the second lead wire 242 with the second portion 138 of the conductive trace 110 of the medical patch 102.

The connector 220 can include a hinged connection between the first and second clamping members 222, 228. For example, the first clamping member 222 can include a hinge protrusion 252 received within a recess 253 of the second clamping member 234.

The connector 220 can include a resilient member 254 arranged and sized such that the resilient member 254 is compressed when the connector 220 is in the closed configuration. The compression of the resilient member 254 can cause the resilient member 254 to exert an opening force against at least one of the first clamping member 222 or the second clamping member 228. The compression of the resilient member 254 can increase pressure and/or friction between the first clamping member 222 and the medical patch 100 and/or between the second clamping member 228 and the medical patch 100. Such increased pressure and/or friction can improve the ability of the connector 220 to retain the medical patch 100 in the connector 220.

II. Applications

The connectors 120, 220 can be used to provide electrical connection with a variety of medical patches 100. As one example, the medical patch 100 can be configured to sense extravasation. For instance, the medical patch 100 can be adhered to the patient's skin such that deformation (e.g., bubbling) of the skin (e.g., due to an injection) causes the medial patch 100 to stretch. Stretching of the medical patch 100 can elongate the conductive trace 110 such that an electrical characteristic (e.g., resistance, capacitance, impedance, etc.) can be detected for the conductive trace between the first portion and second portion of the conductive trace. Thus, the connectors 120, 220 described herein can facilitate electrical connection with medical patches 110 configured to detect and/or monitor skin extravasation.

The medical patch 100, however, can be configured to detect a variety of other skin and/or patient characteristics, such as temperature, moisture (perspiration), blood oxygen level, pulse rate, blood pressure. Further the conductive trace 110 of the medical patch 100 can have a variety of other suitable configurations to detect other suitable electrical characteristics. It should be understood that the presently disclosed connector 120, 220, can be used to facilitate physical and/or electrical connection with any suitable medical patch. Thus, the connectors 120, 220 described herein can facilitate electrical connection with medical patches 110 configured to detect a variety of skin and/or patient properties.

These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A medical sensor patch connector assembly comprising:
    a medical patch having a first side, a second side opposite the first side, and a hole connecting the first side and the second side; and
    a connector comprising:
        a first clamping member having a first contact surface in contact with the first side of the medical patch and a tab protruding through the hole in the medical patch; and
        a second clamping member having a second contact surface in contact with the second side of the medical patch,
    wherein at least one of the first contact surface or the second contact surface of the connector comprises a conductive layer that is in contact with the medical patch.

2. The medical sensor patch connector assembly of claim 1, wherein the second clamping member is engaged with the tab of the first clamping member.

3. The medical sensor patch connector assembly of claim 1,
    wherein the medical patch comprises a conductive layer, and wherein the conductive layer of the connector is in contact with the with conductive layer of the medical patch.

4. The medical sensor patch connector assembly of claim 1, wherein the connector comprises a hinged connection between the first clamping member and the second clamping member.

5. The medical sensor patch connector assembly of claim 1, wherein the first clamping member comprises an arm configured to engage the second clamping member and retain the medical sensor patch connector assembly in a closed configuration.

6. The medical sensor patch connector assembly of claim 1, further comprising a resilient member between the first clamping member and the second clamping member configured to exert an opening force against at least one of the first clamping member or second clamping member.

7. The medical sensor patch connector assembly of claim 1, wherein the connector comprises one or more guide rails configured to align the tab with the hole in the medical patch.

8. The medical sensor patch connector assembly of claim 1, wherein:
    at least one of the first side or the second side of the medical patch comprises a first conductive trace and a second conductive trace; and
    the conductive layer of the at least one of the first contact surface or the second contact surface of the connector comprises a first conductive trace in contact with the first conductive trace of the medical patch and a second conductive trace in contact with the second conductive trace of the medical patch.

9. The medical sensor patch connector assembly of claim 8, further comprising a first lead wire coupled to the first conductive trace of the connector and a second lead wire coupled to the second conductive trace of the connector.

10. A medical sensor patch connector comprising:
    a first clamping member comprising a first contact surface, an arm, and a tab protruding perpendicularly with respect to the first contact surface; and
    a second clamping member comprising a second contact surface and a hinged connection with the first clamping member such that the first contact surface can be arranged opposite and parallel with the second contact surface;
    wherein the tab of the first clamping member is configured to protrude through a hole in a medical patch to retain the medical patch between the first contact surface and the second contact surface when the medical sensor patch connector is in a closed configuration in which at least one of the first contact surface of the first clamping member or the second contact surface of the second clamping member contacts the medical sensor patch, and
    wherein the arm of the first clamping member is configured to engage the second clamping member to retain the medical sensor patch connector in the closed configuration.

11. The medical sensor patch connector of claim 10, wherein the second clamping member is configured to engaged with the tab of the first clamping member.

12. The medical sensor patch connector of claim 10, wherein at least one of the first contact surface or the second contact surface of the connector comprises a conductive layer that is configured to contact the medical patch.

13. The medical sensor patch connector of claim 10, wherein at least one of the first contact surface or the second contact surface of the connector comprises a conductive layer that is configured to contact a conductive trace of the medical patch.

14. The medical sensor patch connector of claim 10, further comprising a resilient member between the first clamping member and the second clamping member and configured to exert an opening force against at least one of the first clamping member or second clamping member when the medical sensor patch connector is in a closed configuration.

15. The medical sensor patch connector of claim 10, wherein:
    at least one of the first contact surface or the second contact surface of the connector comprises a first conductive trace in contact with the first conductive trace of the medical patch and a second conductive trace in contact with the second conductive trace of the medical patch.

16. The medical sensor patch connector of claim 15, further comprising a first lead wire coupled to the first conductive trace of the connector and a second lead wire coupled to the second conductive trace of the connector.

17. A method of forming a medical sensor patch connector assembly, the method comprising:
    providing a first clamping member including a first contact surface and a tab protruding perpendicularly with respect to the first contact surface;
    attaching a second clamping member to the first clamping member at a hinged connection such that a first contact surface of the first clamping member can be arranged opposite and parallel with a second contact surface of the second clamping member and such that the tab of the first clamping member extends perpendicular to the second contact surface; and arranging a medical patch between the first contact surface and second contact surface, wherein at least one of the first contact surface or the second contact surface comprises a conductive layer that is in contact with the medical patch.

18. The method of claim 17, further comprising:

moving the first clamping member towards the second clamping member such that the tab of the of the first clamping member extends through a hole defined by the medical patch.

19. A medical sensor patch connector assembly comprising:
- a medical patch having a first side, a second side opposite the first side, and a hole connecting the first side and the second side; and
- a connector comprising:
  - a first clamping member having a first contact surface in contact with the first side of the medical patch and a tab protruding through the hole in the medical patch;
  - a second clamping member having a second contact surface in contact with the second side of the medical patch; and
  - a resilient member between the first clamping member and the second clamping member configured to exert an opening force against at least one of the first clamping member or second clamping member.

* * * * *